United States Patent
Fuhr et al.

(10) Patent No.: US 9,234,630 B2
(45) Date of Patent: Jan. 12, 2016

(54) METHOD AND DEVICE FOR SUPPLYING LIQUIDS TO ANALYSIS UNITS AND LIQUID HANDLING SYSTEMS

(75) Inventors: Martin Fuhr, Tönisvorst (DE); Stefan Oberbörsch, Aachen (DE); Martin Metzger, Isny (DE); Manfred Lorenz, Tübingen (DE)

(73) Assignees: GRÜNENTHAL GMBH, Aachen (DE); NEVOLAB GMBH, Maierhöfen (DE)

( * ) Notice: Subject to any disclaimer, the term of this patent is extended or adjusted under 35 U.S.C. 154(b) by 257 days.

(21) Appl. No.: 13/817,053

(22) PCT Filed: Aug. 4, 2011

(86) PCT No.: PCT/EP2011/063419
§ 371 (c)(1),
(2), (4) Date: Feb. 14, 2013

(87) PCT Pub. No.: WO2012/022620
PCT Pub. Date: Feb. 23, 2012

(65) Prior Publication Data
US 2013/0139894 A1   Jun. 6, 2013

(30) Foreign Application Priority Data
Aug. 17, 2010  (EP) ..................... 10173023

(51) Int. Cl.
*F17D 1/08* (2006.01)
*G01F 23/20* (2006.01)
*G01G 17/06* (2006.01)
*G01N 30/32* (2006.01)
*G01N 35/10* (2006.01)

(52) U.S. Cl.
CPC *F17D 1/08* (2013.01); *G01F 23/20* (2013.01); *G01G 17/06* (2013.01); *G01N 30/32* (2013.01);
(Continued)

(58) Field of Classification Search
CPC .......... F17D 1/08; G01F 23/20; G01G 17/06; G01N 35/1095; G01N 30/32; G01N 2030/324; Y10T 137/0318; Y10T 137/7287
USPC .............. 73/61.52, 61.55, 61.56; 137/1, 386; 210/101, 198.2
See application file for complete search history.

(56) References Cited

U.S. PATENT DOCUMENTS 3,926,809 A * 12/1975 Jones ......................... 210/198.2
4,116,046 A * 9/1978 Stein ............................ 73/61.55
(Continued)

FOREIGN PATENT DOCUMENTS

DE   10 2007 058718 A1   6/2009
EP        1 376 121 A1    1/2004
(Continued)

OTHER PUBLICATIONS

English translation of International Search Report dated Aug. 22, 2011.

*Primary Examiner* — Daniel S Larkin
(74) *Attorney, Agent, or Firm* — Norris McLaughlin & Marcus, P.A.

(57) ABSTRACT

The invention relates to a method for supplying at least one analysis apparatus with at least one liquid. In the method, the liquid is kept available in a storage tank, from where it is transported into at least one buffer tank. The liquid is fed to the analysis apparatus from the buffer tank, whose filling level is monitored. Here, the buffer tank is arranged above the analysis apparatus and the storage tank is arranged below the analysis apparatus. The invention also relates to a device for carrying out this method as well as to an analysis apparatus in which this device is employed.

13 Claims, 3 Drawing Sheets

(52) U.S. Cl.
CPC ...... *G01N 35/1095* (2013.01); *G01N 2030/324* (2013.01); *Y10T 137/0318* (2015.04); *Y10T 137/7287* (2015.04)

(56) References Cited

U.S. PATENT DOCUMENTS

| | | | |
|---|---|---|---|
| 4,364,263 A | * | 12/1982 | Sankoorikal et al. ........ 73/61.56 |
| 4,374,656 A | * | 2/1983 | Schrenker et al. .............. 96/194 |
| 4,728,434 A | * | 3/1988 | Trafford ........................ 210/656 |
| 4,994,180 A | | 2/1991 | Sims et al. |
| 5,112,492 A | * | 5/1992 | Ransohoff .................... 210/656 |
| 5,397,467 A | * | 3/1995 | Morgan et al. ............. 210/198.2 |

FOREIGN PATENT DOCUMENTS

| | | |
|---|---|---|
| EP | 1 710 004 A2 | 10/2006 |
| WO | 01 51920 A2 | 7/2001 |

* cited by examiner

METHOD AND DEVICE FOR SUPPLYING LIQUIDS TO ANALYSIS UNITS AND LIQUID HANDLING SYSTEMS

PRIORITY CLAIM

This application is a 371 of PCT/EP2011/063419, filed Aug. 4, 2011, which claims foreign priority benefit under 35 U.S.C. §119 of the European Patent Application No. 10173023.2 filed Aug. 17, 2010, the disclosures of which are incorporated herein by reference.

BACKGROUND OF THE INVENTION

1. Field of the Invention

The invention relates to a method for supplying analysis apparatuses and liquid-handling systems with liquids that are kept available in storage tanks.

The invention also relates to a device for carrying out such a method.

2. Description of Related Art

Examples of analysis apparatuses that work with liquids include column chromatographs, whose mode of operation is based on the method of chromatography. The chromatography method is widespread, particularly in chemistry, and allows the separation of substance mixtures through the differential partitioning of their individual constituents between a stationary phase and a mobile phase. The chromatography method is employed, for instance, to isolate and purify substances as well as to analyze the composition of substance mixtures in terms of their contents and quantities.

A prerequisite for carrying out the chromatography method is the presence of a stationary phase and a mobile phase. The stationary phase interacts with the individual constituents of the substance mixture, resulting in a separation of the substance mixture into its individual constituents. For this reason, the term separation segment is often employed for the stationary phase that does not move. The substance mixture that is to be processed, however, is placed into the mobile phase which, for purposes of the separation, moves through the stationary phase together with the substance mixture.

In column chromatography, the stationary phase is normally solid and is also referred to as the sorbent or sorption agent. Known sorbents are, for instance, silica gels or polymers. The mobile phase, in contrast, is normally liquid in column chromatography and is also referred to as the eluent or elution agent. Different solvents are used as eluents, depending on the substance mixtures that are to be analyzed.

Eluents are usually highly flammable and sometimes also toxic hazardous materials that, together with air, can form an explosive atmosphere, which is why they must be stored in safety cabinets so as to comply with the stipulations of the German Chemical Law. These safety cabinets ensure not only safe storage but also prevent vapors from escaping into the surroundings.

One of the most frequently employed special methods for column chromatography is high performance liquid chromatography (HPLC) as a form of liquid chromatography (LC). High performance liquid chromatography makes use of hollow tubes as separation or chromatography columns, which are filled with the stationary phase and through which the eluent moves as the mobile phase. The solution that flows out of the separation column after the separation is called the eluate, which is fed to a downstream detection system for analysis purposes.

A refinement of high performance liquid chromatography is ultra high performance liquid chromatography (UHPLC), which has a far better performance than high performance liquid chromatography and which likewise works with separation columns.

In order to separate a substance mixture into its individual constituents, in high performance liquid chromatography, the eluent is normally pumped through the separation column. Supply systems with HPLC pumps are known for this purpose. On the low-pressure side of these HPLC pumps, the eluent is taken from a storage tank that is normally arranged above the HPLC pumps, and, on the high-pressure side of the HPLC pumps, the eluent is then moved through the separation column. Towards this end, the eluent is kept available in the storage tank without being pressurized.

The familiar supply systems, however, have several drawbacks. On the one hand, with these supply systems, the storage of the eluent at times poses safety risks and potential health hazards for the operators while, on the other hand, only a limited amount of eluent is available in a storage tank due to restrictions on the maximum storage quantity permitted. As a result, however, autonomous and automated analysis operation employing high performance liquid chromatography is not possible.

For this reason, it is also a known procedure to connect two or more storage tanks to each other in order to attain an optimized supply. This, however, calls for the use of additional components such as, for instance, pumps, valves, sensors or fittings, all of which come into contact with the eluent. The eluting power of the eluent, however, increases the potential risk of contamination occurring in the eluent, which can possibly falsify or even invalidate the analysis results for the substance mixtures that are to be analyzed.

SUMMARY OF THE INVENTION

Before this backdrop, it is the objective of invention to put forward a simple, safe and reliable method for supplying analysis apparatuses with liquids, which ensures a continuous supply of the analyses apparatuses with liquids as well as a safe storage of the liquids, and which meets the requirements of the German Chemical Law. Moreover, the potential health risk for operators should be reduced or eliminated. Furthermore, the risk of the occurrence of contaminated liquids and thus of falsified or invalidated analysis results should be markedly reduced.

Another objective of the invention is to put forward an appropriate device for carrying out the method as well as an appertaining analysis apparatus.

The objective is achieved by a method having the features described hereinbelow. The objective is also achieved by a device also described hereinbelow. Moreover, the objective is achieved by an analysis apparatus also described hereinbelow.

The invention puts forward a method for supplying at least one analysis apparatus with at least one liquid. In this method, the liquid is kept available in a storage tank, from where it is transported into at least one buffer tank. The liquid is fed to the analysis apparatus from the buffer tank whose filling level of liquid is monitored. In this context, the buffer tank is arranged above the analysis apparatus and the storage tank is arranged below the analysis apparatus.

This method ensures that, through the use of a buffer tank in which small quantities of the liquid are kept available for the analysis apparatus, the storage tank holding larger quantities of the liquid can be stored separately in a safety cabinet.

Monitoring of the filling level and automatic regulation serve to ensure that there is always sufficient liquid available for the analysis apparatus.

DETAILED DESCRIPTION OF THE INVENTION

One embodiment of the method provides that the storage tank is pressurized and that the liquid is transported from the storage tank into the buffer tank via a riser. A gas is used for the pressurization. This dispenses with the need for various pumps, valves, sensors or fittings for withdrawing the liquid from the storage tank, and it reduces the risk of possible contamination of the liquid since then only a few chemically resistant individual parts are employed in the supply system.

In one embodiment of the method, the liquid in the buffer tank is made available to the analysis apparatus without being pressurized. Just the height difference resulting from the arrangement of the buffer tank above the analysis apparatus gives rise to a slight excess pressure at the inlet of the pump that supplies the analysis apparatus with liquid. This excess pressure minimizes the suction output of this pump accordingly.

A refinement of the method is characterized in that, in order to monitor the filling level of liquid in the buffer tank, the weight of the buffer tank is determined. The determination of the weight of the buffer tank provides the basis for a gravimetric determination of the filling level by means of which the volume and thus the filling level of liquid in the buffer tank can be quickly and easily ascertained.

One embodiment of the invention describes that measured data about the buffer tank is acquired and evaluated by an electronic unit. This measured data constitutes the filling-level data about the liquid in the buffer tank.

In one embodiment of the method, the electronic unit emits a signal when the filling level of liquid in the buffer tank falls below a prescribed limit value. This signal is considered as an indication that the buffer tank needs to be filled from the storage tank from the storage tank in order to prevent the analysis apparatus from running empty and to ensure a continuous supply of liquid to the analysis apparatus.

One refinement of the method provides that the buffer tank is alternately supplied from one of at least two storage tanks. In one embodiment of the method, the buffer tank is filled from the other storage tank while one storage tank is being replaced. If the gravimetric determination of the filling level did not show any change or further drop in the filling level of liquid in the buffer tank within a prescribed time interval, then a switch is made from the presumably empty storage tank to the other storage tank. The empty storage tank can then be replaced during the ongoing analysis procedure. Since there is always one full storage tank on hand to fill the buffer tank, it can be reliably prevented that the analysis apparatus runs empty.

The invention also puts forward a device for supplying at least one analysis apparatus with at least one liquid that is kept available in at least one storage tank. The device has at least one buffer tank that is arranged above the analysis apparatus. In contrast, the storage tank is arranged below the analysis apparatus. The liquid can be transported from the storage tank into the buffer tank and can also be fed from the buffer tank to the analysis apparatus. The device also has a measuring instrument that is configured to monitor the filling level of liquid in the buffer tank.

Due to the use of storage tanks and buffer tanks as well as to their arrangement with respect to the analysis apparatus, this device provides a supply system for liquids that allows storage tanks containing liquids to be kept in intermediate storage in a regulation-compliant safety cabinet. Moreover, the monitoring of the filling level of liquid in the buffer tank allows an automatic regulation of the filling level. This means that this device protects the analysis apparatus from running empty. Excess pressure in the supply system can be appropriately ruled out by using a buffer tank equipped with an overflow. Moreover, the device is easy to maintain since it employs a buffer tank that is arranged separately from the storage tank.

In one embodiment of the device, the storage tank and the buffer tank are connected to each other via a riser. Through the application of pressure, the liquid can be fed from the storage tank arranged below the analysis apparatus via this riser into the buffer tank arranged above the analysis apparatus.

A refinement of the device is characterized in that the measuring instrument for monitoring the filling level of liquid in the buffer tank is configured as a set of scales. With these scales, the filling level of liquid in the buffer tank can be measured quickly and simply by means of a gravimetric determination of the filling level.

One embodiment of the device provides that the measuring instrument is connected to an electronic unit for evaluating measured data. This measured data constitutes filling-level data about the liquid in the buffer tank.

In one embodiment of the device, the buffer tank is configured as a closed tank that has at least one inlet and one outlet for the liquid. This closed buffer tank ensures that the entire supply system is configured as a closed system, so that it cannot be influenced from the outside.

One embodiment of the device describes that the device has at least two storage tanks and that the buffer tank can be filled alternately from one of the storage tanks. The use of two storage tanks means that the filling of the buffer tank does not have to be interrupted while an empty storage tank is being replaced by a full storage tank, since the buffer tank can be filled from the other storage tank during this time. This allows a continuous supply of the analysis apparatus with liquid.

In addition, the invention also put forwards an analysis apparatus comprising at least one device having the described features for supplying the analysis apparatus with at least one liquid.

Therefore, the method and the device for supplying liquid to an analysis apparatus differ from supply systems in which the storage tanks are arranged above the analysis apparatus at the working height of an operator. These conventional supply systems entail a high safety risk since it is very difficult or even impossible to use a safety cabinet to safely store the storage tanks containing liquid and arranged above the analysis apparatus.

Thanks to the advantageous use of a buffer tank above the analysis apparatus, which allows the possibility of arranging the storage tank for the liquid below the analysis apparatus, one now achieves a decisive improvement in the safety of the supply system. As a result, the storage tanks can be kept in a regulation-compliant safety cabinet that can be arranged on the floor below the analysis apparatus.

Owing to the arrangement of the storage tanks below the analysis apparatus, there is no longer a need to replace empty storage tanks with full storage tanks at the working height of an operator. This eliminates a potential health hazard for operators since vapors that normally occur during replacement of the storage tanks are reliably prevented from escaping at the working height of the operator.

Moreover, this eliminates the risk that the storage tank might fall from the working height onto the floor or that it might tip over at the working height of the operator during replacement of the storage tanks. Therefore, the associated potentially hazardous situations due to large quantities of escaping liquid can no longer arise.

The risk of contamination of the analysis apparatus by liquid escaping above the analysis apparatus is likewise reduced since now only the buffer tank configured as a closed tank is arranged above the analysis apparatus.

Moreover, the method and the device differ from supply systems having numerous requisite individual parts such as, for instance, pumps, valves, sensors or fittings, all of which can detrimentally affect the purity of the liquids employed. Contamination can occur in the prior-art supply systems, for example, due to the fact that individual parts sometimes contain materials that are not chemically inert such as, for instance, various plastics, out of which the liquid can dissolve certain constituents, for example, plastic extracts like softeners. Furthermore, in order to function properly, some of these individual parts, for instance, valves or fittings, require lubricant oil or grease that might get into the liquid.

Since the method and the device are advantageously characterized by the use of pressurization of the storage tank with a gas, it is possible to dispense with the numerous individual parts that are needed for conventional supply systems. This reduces the number of non-inert materials and thus the potential sources of contamination stemming from the dissolution of constituents from these non-inert materials, and this also means that contamination stemming from lubricant oil or grease is eliminated since the corresponding individual parts are no longer needed.

In addition, the method and the device ensure a continuous supply of liquid to the analysis apparatus since the buffer tank is alternately filled from one of the two storage tanks. Consequently, an empty storage tank can always be replaced while the buffer tank is being filled from the other storage tank. This means that there is always a full storage tank on hand, which effectively prevents the analysis apparatus from running empty.

The above-mentioned as well as additional advantages, special features and practical refinements of the invention will also be described on the basis of the embodiments, which will be illustrated below making reference to the figures.

BRIEF DESCRIPTION OF THE DRAWINGS

These figures show the following:
FIG. 1 schematically shows the example of a storage tank 101, which has been filled with a solvent 102.

Figure 1:
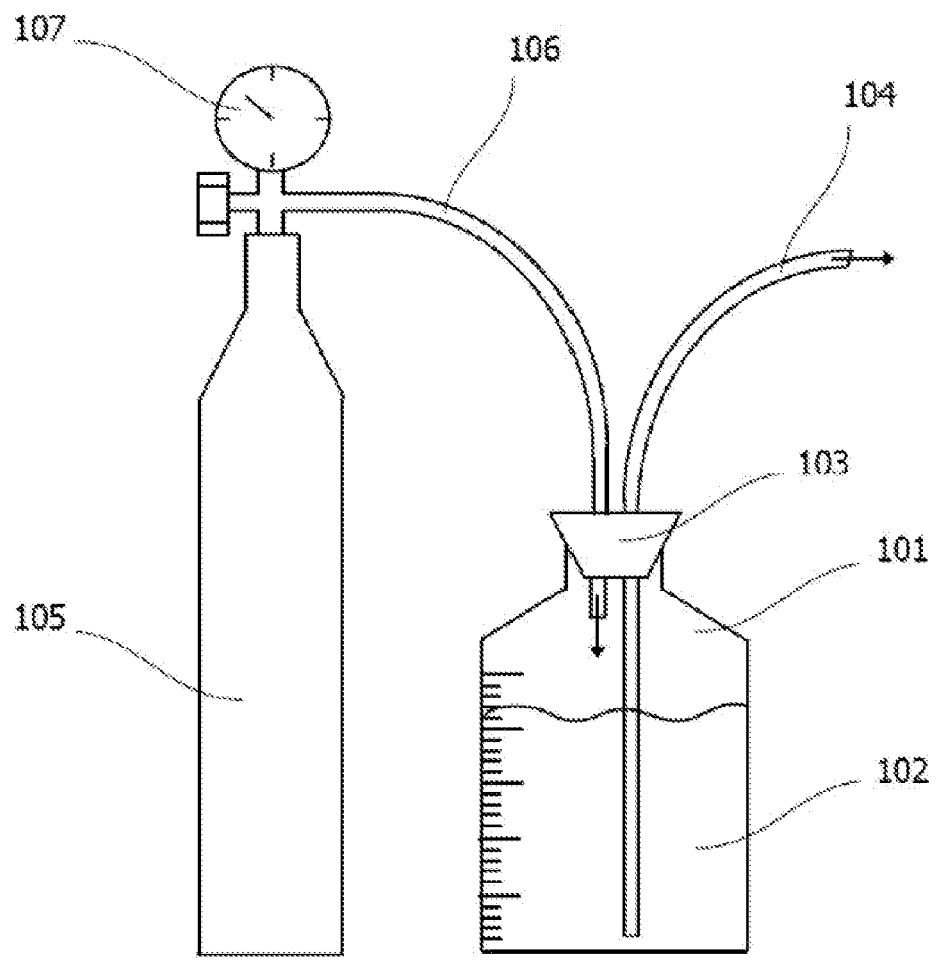
FIG. 1—a pressurized storage tank.

The storage tank 101 is made of a chemically inert material, for instance, break-resistant glass, so that the contamination of the solvent 102 due to the dissolution of individual constituents from the storage tank 101 can be prevented. However, other materials can also be employed for the storage tank 101.

The storage tank 101 is closed by means of a closure 103. This closure 103 is a safety closure that ensures that the storage tank 101 is tightly closed and that a closed system is created in this process. A suitable material for the closure 103 is, for example, polytetrafluoroethylene (PTFE).

A liquid line 104 runs through the closure 103 of the storage tank 101 and leads out of the storage tank 101. The solvent 102 is withdrawn from the storage tank 101 through this liquid line 104.

Perfluoroalkoxyl alkane (PFA), for example, has proven to be suitable as the basic material for the liquid line 104. PFA exhibits a high thermal and chemical resistance. It is flame-resistant and displays a largely inert behavior, thus avoiding contamination of the solvent 102 while it passes through the liquid line 104. However, other materials can also be used for the liquid line 104.

The storage tank 101 is pressurized in order to withdraw the solvent 102. This pressure is generated by means of a gas that is introduced into the storage tank 101 from a pressure cylinder 105 via a pressure-proof gas line 106. The introduced gas then displaces the solvent 102 out of the storage tank 101 into the liquid line 104. The direction of flow of the gas from the pressure cylinder 105 through the gas line 106 into the storage tank 101 as well as the direction of flow of the solvent 102 from the storage tank 101 into the liquid line 104 are indicated accordingly by arrows.

The adjustable pressure with which the gas from the pressure cylinder 105 is introduced into the storage container 101 influences the flow rate of the solvent 102 into the liquid line 104. The higher the gas pressure, the faster the solvent 102 is displaced out of the storage tank 101 into the liquid line 104, and conversely, the lower the gas pressure, the more slowly the solvent 102 is displaced out of the storage tank 101 into the liquid line 104. A pressure regulator 107 with which the pressure can be adjusted is provided on the pressure cylinder 105.

An example of a pressure regulator 107 is an automatic regulating unit. The automatic regulating unit allows the gas pressure and thus the flow rate of the solvent 102 to be adjusted very precisely. However, another possibility is to employ manual operation, which can be realized simply and quickly.

In order to avoid contamination of the solvent 102, the gas recommended for pressurizing the storage tank 101 is an inert gas, for instance, argon as a noble gas. Nitrogen as an unreactive gas also seems suitable. However, other gases are likewise conceivable for pressurizing the storage tank 101.

Figure 2:
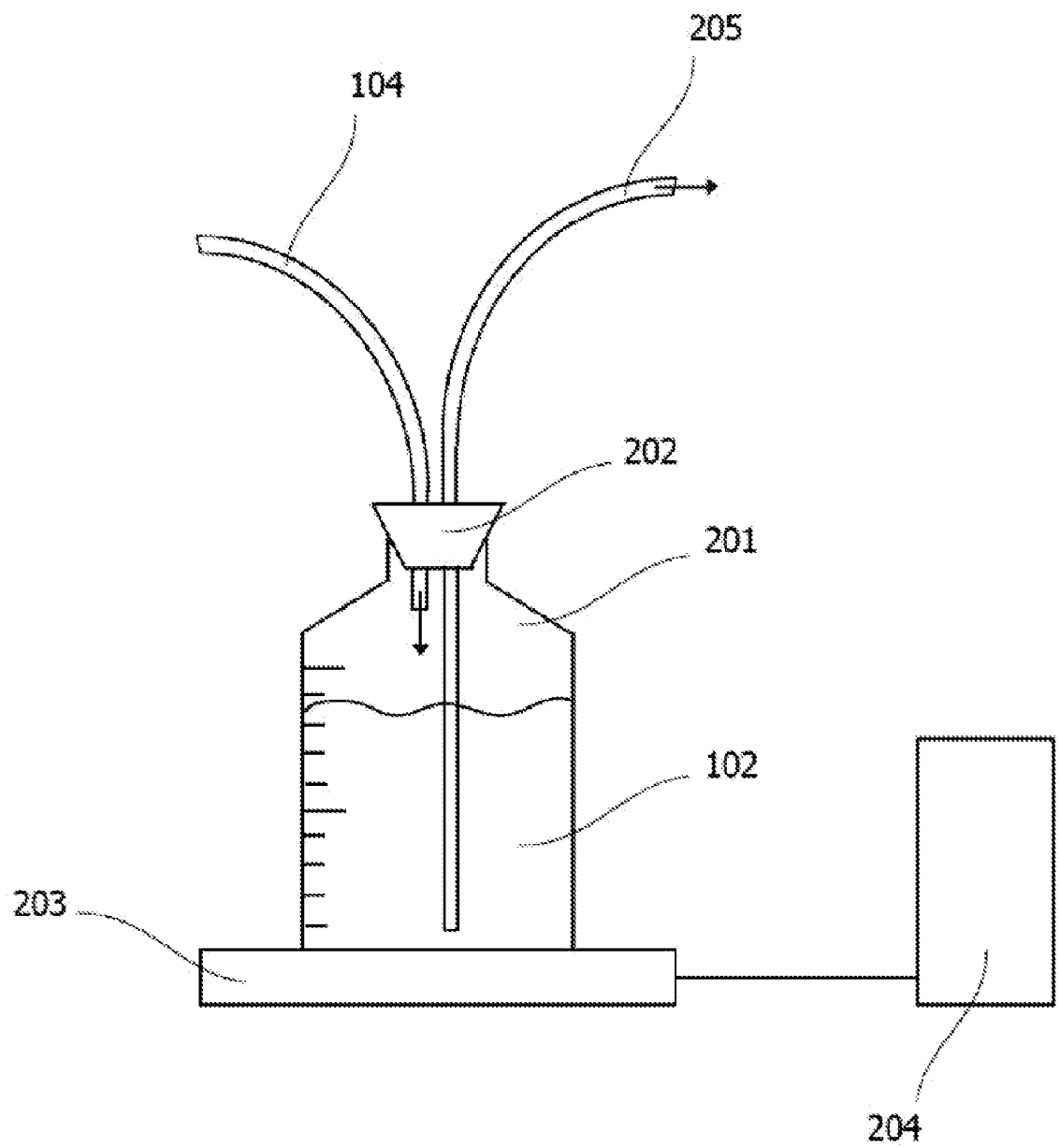
FIG. 2—a buffer tank with a filling-level control unit.

FIG. 2 schematically shows the example of a buffer tank 201 that is filled with solvent 102.

Like the storage tank 101, the buffer tank 201 is also made of a chemically inert material, for instance, break-resistant glass, thus preventing contamination of the solvent 102 due to the dissolution of individual constituents out of the buffer tank 201. However, other materials can also be employed for the buffer tank 201.

A closure 202 is provided for closing the buffer tank 201. The closure 202 is likewise a safety closure that ensures that the buffer tank 201 is tightly closed and that a closed system is thus created. Polytetrafluoroethylene (PTFE), for example, is likewise a suitable material for the closure 202.

The liquid line 104 runs through the closure 202 of the buffer tank 201 and leads into the buffer tank 201. The solvent 102 from the storage tank 101 is filled into the buffer tank 201 through the liquid line 104.

An overflow (not shown here) can be arranged either on the buffer tank 201 or on the closure 202, and it reliably prevents excess pressure from building up in the buffer tank 201.

For purposes of determining the filling level of solvent 102 in the buffer tank 201, the buffer tank 201 is placed onto a measuring instrument used for a sensor-based filling-level control such as, for instance, a set of scales 203.

The set of scales 203 is a measuring instrument for determining the weight, which can be done by means of the weight force. An example of a recommended set of scales 203 is a set of electronic tabletop scales, which are sturdy, accurate and quickly readable. Moreover, the measured data of electronic tabletop scales can be processed and evaluated electronically.

The set of scales 203 implements a gravimetric determination of the filling level in which the filling level of solvent 102 in the buffer tank 201 is derived from the determined weight of the buffer tank 201 containing the solvent 102. For this purpose, the set of scales 203 continuously measures the weight of the buffer tank 201 containing the solvent 102, after which the measured data acquired is forwarded to an electronic unit 204, where it is processed.

An example of an electronic unit 204 that can be used is a known system for data processing, namely, a computer with a processor and a memory.

Various types of data can be stored in the electronic unit 204 in order to determine the filling level of solvent 102. This data includes, for instance, the tare of the buffer tank 201 as well as the specific weight of the solvent 102 used. This data can be employed to determine the filling level of solvent 102 in the buffer tank 201 in the following manner:

$$V = \frac{(F - M * g)}{G}$$

wherein the individual formula symbols stand for the following:

V: volume [m$^3$] of the solvent 102
F: measured weight force [N]
M: tare [kg] of the buffer tank 201
g: gravitational acceleration [9.81 m/s$^2$]
G: specific weight [Nm$^3$] of the solvent 102

As an alternative, a simplified method can be employed to determine the filling level of solvent 102 in the buffer tank 201. In this simplified method, the empty buffer tank 201 is weighed and the ascertained weight is defined as the lower calibration point. The weight of the buffer tank 201 that is filled with a defined quantity, for example, 100 ml, serves to determine the upper calibration point. Both calibration points are stored accordingly in the electronic unit 204. Owing to the existing linear dependence relationship, these two calibration points can then be used to derive the filling level of solvent 102 in the buffer tank 201 on the basis of the measured weight force.

In order for the solvent 102 to be withdrawn from the buffer tank 201, another liquid line 205 passes through the closure 202. The solvent 102 can be withdrawn from the buffer tank 201 via this liquid line 205 without being pressurized so that it can be used further. The direction of flow of the solvent 102 through the liquid line 104 into the buffer tank 201 as well as the direction of flow of the solvent 102 from the buffer tank 201 into the liquid line 205 are indicated here accordingly by arrows.

Figure 3:
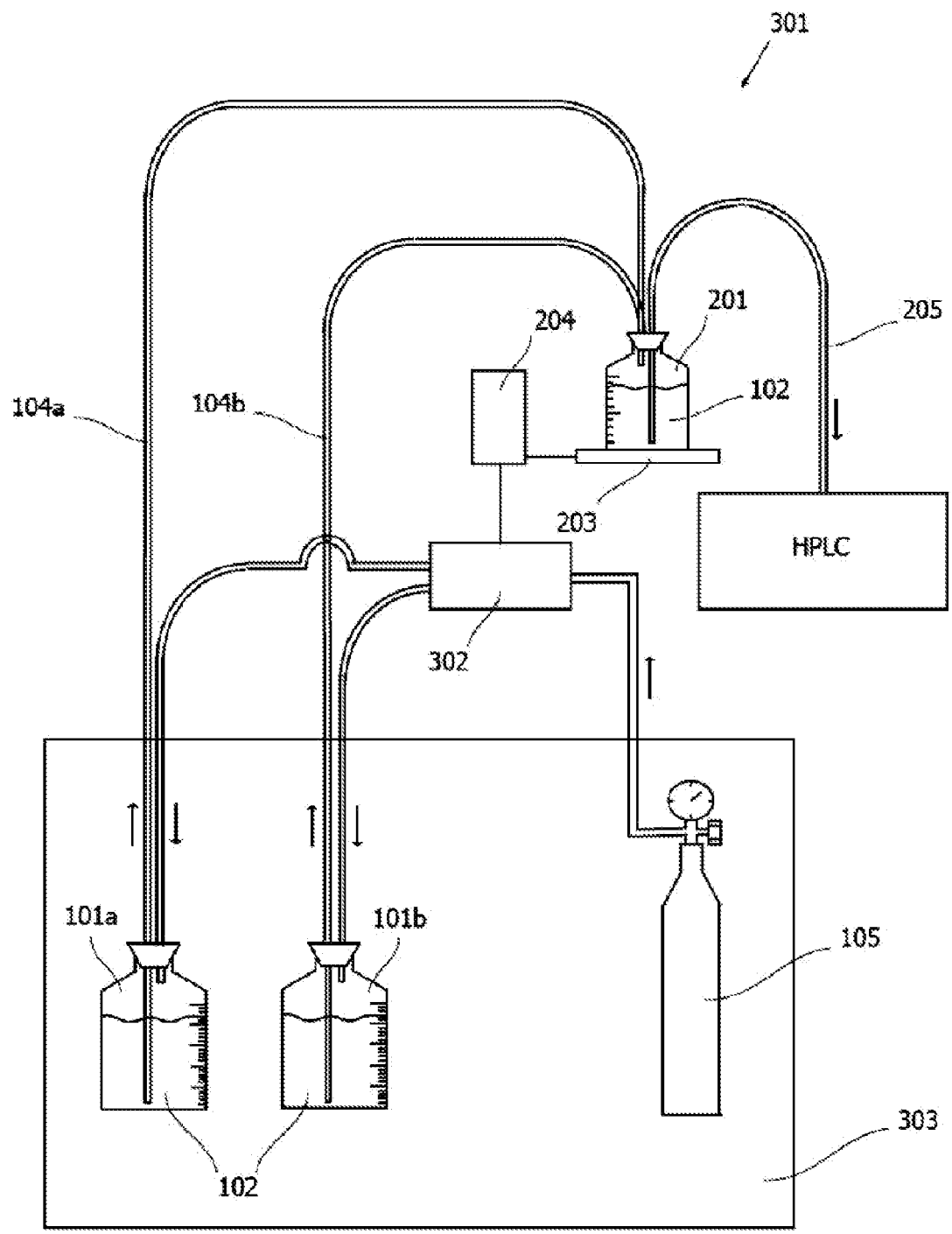
FIG. 3—a solvent supply system with two storage tanks.

By way of an example, FIG. 3 shows a solvent supply device 301 as a device to feed solvent 102 from a buffer tank 201 to an HPLC analysis apparatus, comprising two storage tanks 101a and 101b. With this solvent supply device 301, the storage tanks 101a and 101b are arranged below the HPLC analysis apparatus, while the buffer tank 201 is arranged above the HPLC analysis apparatus.

The buffer tank 201 is filled with solvent 102 alternately from the two storage tanks 101a and 101b. For this purpose, a pressure switchover means 302 is provided upstream from the two storage tanks 101a and 101b, said pressure switchover means 302 controlling the feed of solvent 102 from one of the two storage tanks 101a or 101b.

The buffer tank 201 is first filled with solvent 102 from the storage tank 101a. For this purpose, the storage tank 101a is pressurized with gas from the pressure cylinder 105. The gas pressure causes the solvent 102 to rise through the liquid line 104a into the buffer tank 201. The liquid line 104a is configured here as a riser since the storage tank 101a is arranged below the buffer tank 201.

Instead of the pressure cylinder 105, it is also possible to employ a stationary gas-supply apparatus or a central gas system installed in the building, by means of which the appropriate gas is provided at a regulatable pressure in order to pressurize the storage tanks 101a and 101b. Another alternative is to use a separate pressure cylinder 105 for each of the two storage tanks 101a and 101b.

During the filling procedure with the solvent 102, the set of scales 203 continuously measures the weight of the buffer tank 201 and relays the data to the electronic unit 204 for evaluation purposes. The filling level of solvent 102 in the buffer tank 201 is determined in the electronic unit 204 on the basis of the measured data acquired. Once a predefined maximum filling level of solvent 102 has been reached in the buffer tank 201, the feed of solvent 102 from the storage tank 101a into the buffer tank 201 is stopped.

The solvent 102 can then be fed from the buffer tank 201 to the HPLC analysis apparatus by means of an HPLC pump. The solvent 102 serves in the HPLC analysis apparatus, for example, as the mobile phase during the execution of analyses by means of high performance liquid chromatography. While the analyses are being conducted, the required quantity of solvent 102 is fed from the buffer tank 201 to the separation columns of the high performance liquid chromatograph. In order for a sufficient quantity of solvent 102 to always be available in the buffer tank 201 for the analyses, the quantity of solvent 102 withdrawn from the buffer tank 101a is replenished via the liquid line 104a.

The buffer tank 201 can be filled with solvent 102 either continuously or discontinuously. In the case of a continuous filling of the buffer tank 201, the rate of withdrawal of solvent 102 from the buffer tank 201 corresponds to the feed rate of solvent 102 from the storage tank 101a into the buffer tank 201. In contrast, in the case of discontinuous filling of the buffer tank 201, solvent 102 is only fed once again from the storage tank 101a into the buffer tank 201 after the filling level of solvent 102 has fallen below a defined minimum value. Once the defined maximum filling level of solvent 102 in the buffer tank 201 has been reached, the feed of solvent 102 from the storage tank 101a into the buffer tank 201 is stopped again.

If the storage tank 101a has been emptied while analyses are being conducted, and if this means that no more solvent 102 can be fed into the buffer tank 201, then the filling level of solvent 102 in the buffer tank 201 drops. This also causes the measured values for the weight of the buffer tank 201 to drop.

If the filling level of the solvent 102 has fallen below a predefined limit value that is stored in the electronic unit 204, and if this value is still below the minimum filling level in case of discontinuous filling, then the electronic unit 204 emits a signal. This signal can be, for example, an acoustic or visual signal. A combination of both types of signal is also possible. Depending on its type, the signal is then emitted either by a loudspeaker or by a visual display, or is shown on a monitor.

The signal of the electronic unit 204 thus indicates that it is necessary to fill solvent 102 into the buffer tank 201. As an alternative, the signal of the electronic unit 204 can also be considered as an indication that the storage tank 101a is empty and that it has to be replaced by a full storage tank 101a.

By emitting the signal, the electronic unit 204 also emits a signal to the gas switchover means 302. This signal switches the feed of the solvent 102 into the buffer tank 201 over from the storage tank 101a to the storage tank 101b. For this purpose, a valve in the gas switchover means 302 is switched over and the pressurization of the storage tank 101b via the pressure cylinder 105 is started.

When two separate pressure cylinders 105 are employed for the two storage tanks 101a and 101b, the switchover from the pressure cylinder 105 for the storage tank 101a to the other pressure cylinder 105 for the storage tank 101b takes place simultaneously.

The pressurization of the storage tank 101b causes the solvent 102 to rise in the buffer tank 201 via the liquid line 104b, which is likewise configured as a riser. This once again raises the filling level in the buffer tank 201 accordingly.

Now the empty storage tank 101a can be replaced by a full one without having to interrupt the ongoing analyses being conducted with the HPLC analysis apparatus. This switchover procedure between the two storage tanks 101a and 101b for replacing an empty storage tank 101a or 101b can be repeated as often as desired. Whenever one of the two storage tanks 101a or 101b is empty, the valve in the gas switchover means 302 switches over to the other storage tank 101a or 101b, and the empty storage tank 101a or 101b can be replaced. This ensures that a full storage tank 101a or 101b is available at all times, so that there is always a continuous supply of solvent 102 for the HPLC analysis apparatus, thus effectively preventing the HPLC analysis apparatus from running empty.

For safety reasons, the storage tanks 101a or 101b are accommodated in a safety cabinet 303 that rests on the floor and that is designed in accordance with the stipulations of the German Chemical Law. This safety cabinet 303 has an exhaust system for vapors generated by the solvent 102 and it is appropriately explosion-proof.

Therefore, the replacement of the storage tanks 101a or 101b no longer takes place at the working height of the operator, but rather below the HPLC analysis apparatus at floor level. This enhances the safety and reduces the health hazard for the operator in question. The storage tanks 101a or 101b can no longer fall from the working height to the floor, and the exhaust system installed in the safety cabinet 303 reduces the concentration of escaping vapors when the storage tanks 101a or 101b are being replaced.

Aside from the storage tanks 101a and 101b, it also possible to store waste containers for the eluate of the HPLC analysis apparatus in the safety cabinet 303. However, the waste containers for the eluate can also be stored in another safety cabinet.

The safety of the operators and also of the HPLC analysis apparatus can be further enhanced in that the buffer tank 201 is permanently installed and can thus be secured against falling over. Since it is not necessary to replace the buffer tank 201, there is even less of a health hazard for the operators.

The buffer tank 201 can be used to supply one or more HPLC analysis apparatuses. All that is necessary for this purpose is to dimension the buffer tank 201 and the liquid lines 104a and 104b appropriately.

It is likewise conceivable for both storage tanks 101a and 101b to be filled with different liquids. By simultaneously feeding the liquids from both storage tanks 101a and 101b into the buffer tank 201, the liquids in the buffer tank 201 are mixed, for instance, to form a solvent 102 that can then be made available to the HPLC analysis apparatus.

The device 301 and the associated method for supplying an HPLC analysis apparatus with a solvent 102 provide a simple, safe and reliable supply system for analysis apparatuses and liquid-handling systems. The device 301 and the method ensure a continuous supply to the analysis apparatuses as well as regulation-compliant storage of the solvent 102, and also a supply of pure solvent 102 without contamination that could falsify the analysis results. Moreover, the device 301 and the method offer the possibility to appropriately comply with the requirements of the German Chemical Law and to minimize potential health hazards for operators.

LIST OF REFERENCE NUMERALS 101, 101a, 101b storage tanks
102 solvent/liquid
103 closure
104, 104a, 104b liquid line/riser
105 pressure cylinder
106 gas line
107 pressure regulator
201 buffer tank
202 closure
203 set of scales
204 electronic unit
205 liquid line
301 solvent-supply system
302 pressure switchover means
303 safety cabinet

The invention claimed is:

1. A method for supplying at least one analysis apparatus with at least one liquid, whereby the liquid is kept available in at least one storage tank, comprising transporting the at least one liquid from the at least one storage tank into at least one buffer tank, and in that the at least one liquid is fed from the at least one buffer tank- to the analysis apparatus, whereby the at least one buffer tank is arranged above the at least one analysis apparatus and the at least one storage tank is arranged below the at least one analysis apparatus, and monitoring the filling level of the at least one liquid in the at least one buffer tank visually or via a measuring instrument configured to monitor the filling level of the at least one liquid;
wherein
the at least one storage tank is pressurized, whereby a gas is used for the pressurization, and the at least one liquid is transported from the at least one storage tank into the at least one buffer tank via a riser.

2. The method according to claim 1,
wherein
the at least one liquid in the at least one buffer tank is made available to the at least one analysis apparatus without being pressurized.

3. The method according to claim 1,
wherein,
in order to monitor the filling level of the at least one liquid in the at least one buffer tank, the weight of the buffer tank is determined by a set of scales.

4. The method according to claim 1,
wherein
measured data about the at least one buffer tank is acquired and evaluated by an electronic unit, whereby this measured data constitutes the filling-level data about the at least one liquid in the at least one buffer tank.

5. The method according to claim 1,
wherein
the electronic unit emits a signal when the filling level of the at least one liquid in the at least one buffer tank falls below a prescribed limit value, whereby this signal is considered as an indication that the at least one buffer tank needs to be filled.

6. The method according to claim 1,
wherein
the at least one buffer tank is alternately supplied from one of at least two storage tanks.

7. The method according to claim 5,
wherein
the at least one buffer tank is filled from one storage tank while a second storage tank is being replaced.

8. A device for supplying at least one analysis apparatus with at least one liquid, whereby the liquid is kept available in at least one storage tank being pressurized, whereby a gas is used for the pressurization,
the device comprising at least one buffer tank, whereby the buffer tank is arranged above the at least one analysis apparatus and the at least one storage tank is arranged below the at least one analysis apparatus, and whereby the at least one liquid is transported from the at least one storage tank into the at least one buffer tank via a riser, and whereby the at least one liquid is fed from the at least one buffer tank to the at least one analysis apparatus, and the device further comprising a measuring instrument, whereby the measuring instrument is configured to monitor the filling level of the at least one liquid in the at least one buffer tank.

9. The device according claim 7,
wherein
the measuring instrument for monitoring the filling level of the at least one liquid in the at least one buffer tank is configured as a set of scales.

10. The device according to claim 7,
wherein
the measuring instrument is connected to an electronic unit for evaluating measured data, whereby this measured data constitutes filling-level data about the at least one liquid in the at least one buffer tank.

11. The device according to claim 7,
wherein
the at least one buffer tank is configured as a closed tank that has at least one inlet and one outlet for the at least one liquid.

12. The device according to claim 7,
wherein
the device has at least two storage tanks, whereby the at least one buffer tank can be filled alternately from one of the storage tanks.

13. An analysis apparatus,
comprising at least one device according to claim 7 for supplying the analysis apparatus with at least one liquid.

* * * * *